(12) United States Patent
Jones, Jr. et al.

(10) Patent No.: US 7,863,025 B2
(45) Date of Patent: Jan. 4, 2011

(54) SYNTHESIS OF FATTY ALCOHOL ESTERS OF ALPHA-HYDROXY CARBOXYLIC ACIDS AND THEIR USE AS PERCUTANEOUS ABSORPTION ENHANCERS

(75) Inventors: Gerald S. Jones, Jr., Norwood, MA (US); Joseph P. St. Laurent, Lakeville, MA (US); Scott A. Goodrich, Stoughton, MA (US)

(73) Assignee: Chemic Laboratories, Inc., Canton, MA (US)

( * ) Notice: Subject to any disclaimer, the term of this patent is extended or adjusted under 35 U.S.C. 154(b) by 247 days.

(21) Appl. No.: 11/251,738

(22) Filed: Oct. 17, 2005

(65) Prior Publication Data

US 2006/0084154 A1     Apr. 20, 2006

Related U.S. Application Data

(60) Provisional application No. 60/619,887, filed on Oct. 18, 2004, provisional application No. 60/698,248, filed on Jul. 11, 2005.

(51) Int. Cl.
*C12P 7/64* (2006.01)

(52) U.S. Cl. .................. 435/134; 435/135; 554/174

(58) Field of Classification Search ............... None
See application file for complete search history.

(56) References Cited

U.S. PATENT DOCUMENTS 6,639,095 B1   10/2003   Uang et al.

2002/0055650 A1*   5/2002   Hidaka et al. ............ 560/212

FOREIGN PATENT DOCUMENTS

| ES | 2143940 | 5/2000 |
|---|---|---|
| WO | 2006044926 | 4/2006 |

OTHER PUBLICATIONS

Ramalinga et al., "A mild and efficient method for esterficiaton and transesterification catalyzed by iodine.". Tetrahedron Letters. vol. 43, pp. 879-882, 2002.*

(Continued)

*Primary Examiner*—Deborah D Carr
(74) *Attorney, Agent, or Firm*—Lando & Anastasi, LLP

(57) ABSTRACT

The present invention provides a novel approach for the preparation of fatty alcohol esters of α-hydroxy carboxylic acids. In one form of the invention, the target fatty alcohol ester of α-hydroxy carboxylic acid is produced by converting a lower alkyl ester of α-hydroxy carboxylic acid into a fatty alcohol ester of α-hydroxy carboxylic acid via alcoholysis (i.e., transesterification). The transesterification process is an equilibrium reaction, catalyzed chemically (i.e., with acids or bases) or enzymatically, that is shifted in the desired direction to produce the desired product. One preferred way of shifting the reaction in the direction of the desired product is by reducing the concentration of one of the products (e.g., distillation of a lower-boiling alcohol as soon as it is formed). Another preferred way of shifting the reaction in the direction of the desired product is by increasing the concentration of one of the reactants (e.q., adding more of the starting ester).

56 Claims, 5 Drawing Sheets

OTHER PUBLICATIONS

Torres et al., "Part I. Enzymatic synthesis of lactate and glycolate esters of fatty alcohols", Enzyme and Microbial Techonlogy vol. 25, pp. 745-752, 2002.*

Morrison & oyd, 4$^{th}$ Ed. 1983, pp. 837-838.*

Kayer et al., Journal of Organic Chemistry (1999), 64(18), 6603-6608.*

International Search Report dated Aug. 8, 2006 from International Application No. PCT/US05/37504.

* cited by examiner

SYNTHESIS OF FATTY ALCOHOL ESTERS OF ALPHA-HYDROXY CARBOXYLIC ACIDS AND THEIR USE AS PERCUTANEOUS ABSORPTION ENHANCERS

REFERENCE TO PENDING PRIOR PATENT APPLICATIONS

This patent application claims benefit of:

(i) prior U.S. Provisional Patent Application Ser. No. 60/619,887, filed Oct. 18, 2004 by Gerald S. Jones, Jr. et al. for SYNTHESIS OF DODECYL LACTATE AND RELATED COMPOUNDS AND THEIR USE AS PERCUTANEOUS ABSORPTION ENHANCERS; and (ii) prior U.S. Provisional Patent Application Ser. No. 60/698,248, filed Jul. 11, 2005 by Gerald S. Jones, Jr. et al. for SYNTHESIS OF DODECYL LACTATE AND RELATED COMPOUNDS AND THEIR USE AS PERCUTANEOUS ABSORPTION ENHANCERS The two above-identified patent applications are hereby incorporated herein by reference.

FIELD OF THE INVENTION

This invention relates to transdermal drug delivery in general, and more particularly to a method for the synthesis of fatty alcohol esters of α-hydroxy carboxylic acids for use as percutaneous absorption enhancers.

BACKGROUND OF THE INVENTION

Transdermal drug delivery (TDD) is the delivery of drugs by absorption through the skin and into the body. TDD has become an established, non-invasive route for both the local and systemic administration of drugs.

TDD offers the advantages of smaller drug doses, improved efficacy, reduced toxicity, elimination of first-pass metabolism, minimization of pain, and possible sustained release.

Despite the obvious advantages of TDD, this delivery approach has not been more widely exploited due to the intrinsic barrier properties of the skin. Human skin is made up of two layers, the epidermis (i.e., the outer layer) and the dermis (i.e., the inner layer). The stratum corneum, which is the outermost layer of the epidermis, acts as the main barrier to drug delivery. With the discovery and implementation of an effective means for penetrating this barrier, TDD becomes a more attractive drug delivery option.

The integrity of the stratum corneum can be disrupted (and hence its permeability increased) through the use of sound energy, electrical energy or physical methods. Considerable effort has been concentrated on identifying non-toxic chemical compounds that will interact with the stratum corneum, thereby increasing the potential for drug penetration. These compounds are sometimes referred to as "permeation enhancers", "penetration enhancers" or "absorption enhancers".

A review of the recent patent literature reveals numerous practical examples of permeation enhancers used as transdermal delivery devices, including:

| U.S. Pat. No. | Year | Assignee | Title | Enhancer |
| --- | --- | --- | --- | --- |
| 6699497 | 2004 | Alza | Formulations for the transdermal administration of fenoldopam | lauryl lactate; myristyl lactate |
| 6638981 | 2003 | EpiCept | Topical compositions and methods for treating pain | Transcutol ® P |
| 6582724 | 2003 | Dermatrends | Dual enhancer composition for topical and transdermal drug delivery | Transcutol ® P; Azone ® |
| 6156753 | 2000 | Vivus | Local administration of type III phosphodiesterase inhibitors for the treatment of erectile dysfunction | Azone ®; SEPA ® |
| 6118020 | 2000 | NexMed | Crystalline salts of dodecyl 2-(N,N-dimethylamino)propionate | NexACT ® |
| 6004578 | 1999 | Alza | Permeation enhancers for transdermal drug delivery compositions, devices and methods | lauryl acetate; lauryl lactate |
| 5843468 | 1998 | Alza | Skin permeation enhancer compositions comprising glycerol monolaurate and lauryl acetate | glycerol monolaurate; lauryl acetate |
| 5314694 | 1994 | Alza | Transdermal formulations, methods and devices | lauryl lactate |

Approximately thirty chemical compounds have been routinely used by the pharmaceutical industry as permeation enhancers. Most of these compounds, however, provide only a slight improvement in absorption.

The known and putative permeation enhancers include members of several classes of organic compounds, including:

| Class | Compound(s) |
| --- | --- |
| Alcohols | ethanol; isopropanol; benzyl alcohol |
| Glycols | propylene glycol; diethylene glycol monoethyl ether (Transcutol ®) |
| glycol esters | glycerol monolaurate |
| fatty acids | oleic acid |
| fatty acid esters | isopropyl myristate |
| fatty alcohol esters | lauryl lactate; myristyl lactate; cetyl lactate; dodecyl methacrylate |
| miscellaneous | DMSO; laurocapram (Azone ®); 2-nonyl-1,3-dioxolane (SEPA ®); dodecyl 2-(N,N-dimethylamino) propionate (NexACT ®) |

Most of the permeation enhancers fit a common general structure, which is representative of a non-ionic surface-active agent, i.e., a non-ionic surfactant. The general structure consists of two discrete portions that possess diametrically-opposed physicochemical properties: a polar head and a lipophilic tail. The polar head of the molecule can include one of a variety of functional groups, as listed above; the lipophilic tail consists of a hydrocarbon chain that typically ranges from eight to sixteen carbon atoms in length. FIG. 1 illustrates the structures of eight permeation enhancers (both proprietary and generic) having the aforementioned polar head and lipophilic tail structure.

Of the chemical compounds used as permeation enhancers, one class of compounds in particular—fatty alcohol esters of α-hydroxy carboxylic acids (e.g., alkyl lactates)—has found widespread use in cosmetic and pharmaceutical formulations as humectants and/or emollients. This is particularly true for alkyl lactates where the alkyl group is greater than eight carbon atoms in length (i.e., $>C_8$).

This class of compounds (i.e., fatty alcohol esters of α-hydroxy carboxylic acids)—and specifically dodecyl lactate (also known as lauryl lactate), myristyl lacate and cetyl lactate—has also generated considerable interest for application in TDD due to its permeation enhancing properties.

Esters (including fatty alcohol esters) can be prepared using a variety of traditional techniques. These techniques typically utilize a carboxylic acid (e.g., α-hydroxy carboxylic acid) and alcohol to produce the desired ester.

The following briefly discusses traditional approaches for preparing esters.

Preparation of Esters

Looking next at FIG. 2, most industrial processes for the preparation of esters (i.e., esterification) involve the reaction of a carboxylic acid 5 with an alcohol 10 in the presence of a chemical esterification catalyst 15 to produce an ester 20. Chemical esterification catalyst 15 is generally an acid or a base, e.g., organic sulfonic acid or metal alkylate. One problem with the ester-producing mechanism shown in FIG. 2 is that the esters produced typically contain catalyst residues and by-products, such as difficult-to-remove ethers.

Alternatively, the esterification of a carboxylic acid with an alcohol can be accomplished via an enzymatic process. In this reaction, which is similar to the one illustrated in FIG. 2, an enzyme (most often a lipase) is used in place of the chemical esterification catalyst 15, typically resulting in a cleaner reaction and, possibly, a higher yield of pure product. European Patent No. 0383405 (1990) describes the use of lipase in the esterification of $C_7$-$C_{36}$ monocarboxylic or dicarboxylic acids with $C_2$-$C_8$ alcohols.

FIG. 3 shows a Fischer-type esterification, where carboxylic acid is converted into an ester in the presence of alcohol and an acid catalyst. In FIG. 3, the Fischer-type esterification is illustrated in the context of producing the fatty alcohol ester lauryl lactate. More specifically, an α-hydroxy carboxylic acid 25 (e.g., lactic acid, where R=$CH_3$; α-hydroxypropionic acid) is combined with an alcohol 30 (e.g., dodecanol, where R'=$C_{12}H_{25}$) in the presence of a chemical esterification catalyst 33 to produce lauryl lactate 35 (where R is $CH_3$ and R' is $C_{12}H_{25}$). This is believed to be a common commercial approach for producing lauryl lactate.

One problem with this reaction is the potential reactivity of the α-hydroxy group of the α-hydroxy carboxylic acid 25. As a competitive nucleophile in the esterification reaction, involvement of the α-hydroxy group can result in the formation of polyester (e.g., the polyester 40 shown in FIG. 3). Subsequently, lactonization of the polyester 40 may produce cyclic ester (e.g., the cyclic ester 45 shown in FIG. 3).

Another problem with this reaction is that the lauryl lactate produced by the Fisher-type esterification can contain as much as 5% dodecanol, as well as intermolecular esterification products (carried over from the commercial lactic acid 25), and varying amounts of unidentified polymeric species.

While the resulting lauryl lactate is relatively inexpensive to produce, the equivocal quality is directly related to the use of commercial lactic acid as a starting material in the esterification process. Commercial lactic acid is available as an aqueous solution (~85%), which contains varying amounts of intermolecular esterification products. When subjected to the harsh conditions of esterification, a complex reaction mixture is inevitable, and often results in the formation of various by-products. Whereas esterification of lactic acid with dodecanol can also be accomplished via an arguably milder enzymatic process, the process still necessitates the use of lactic acid as a starting material. Therefore, this process will also yield a low purity lauryl lactate product.

A review of the literature reveals several other approaches for producing alkyl lactates (including lauryl lactate).

For example, the synthesis of lauryl lactate using Dawson phosphotungstic acid catalyst is described in Guangzhou Huaxue 2002, 27(1), 32-33, 55 (Chinese). The abstract to this article reported that, under optimum conditions, the yield was greater than 93%. The purity of the product was not mentioned.

In another example, described in Xiamen Daxue Xuebao, Ziran Kexueban 1997, 36(4), 581-584 (Chinese), various lactate esters were prepared by a Fisher-type esterification. Yields ranged from 81-98%, but the yield for lauryl lactate was not specified in the abstract.

In another example, esters of α-hydroxy carboxylic acids were prepared by an enzymatic approach (with lipase as the enzyme). This study was described in Enzyme and Microbial Technology 1999, 25, 745-752, and it focused on the optimization of reaction conditions for the syntheses of lactate and glycolate esters of fatty alcohols, including lauryl lactate, via esterification of the requisite carboxylic acid. Optimization of the process resulted in the high conversion of lactic acid and dodecanol to lauryl lactate (~96%). Spanish Patent No. ES 2143940, relating to this study, was published in 2000.

While all of the foregoing approaches are capable of producing esters, including fatty alcohol esters and including specifically lauryl lactate, they all yield a relatively impure product. This has proven to be a problem for many applications, including use as a permeation enhancer for TDD.

SUMMARY OF THE INVENTION

One object of the present invention is to provide a new and improved method for making fatty alcohol esters of α-hydroxy carboxylic acids.

A further object of the present invention is to provide a new and improved method for making fatty alcohol esters of α-hydroxy carboxylic acids, wherein the ester is an alkyl lactate.

Still another object of the present invention is to provide a new and improved method for making fatty alcohol esters of α-hydroxy carboxylic acids, wherein the ester is lauryl lactate.

Yet another object of the present invention to provide a method for making fatty alcohol esters of α-hydroxy carboxylic acids that is convenient, efficient, reproducible, and scalable.

And another object of the present invention to provide a method for making fatty alcohol esters of α-hydroxy carboxylic acids, wherein the purity of the product is consistently greater than 95%.

And still another object of the present invention to create a novel family of compounds for use as permeation enhancers.

These and other objects are addressed by the provision and use of the present invention, which provides a novel approach for the preparation of fatty alcohol esters of α-hydroxy carboxylic acids.

In one form of the invention, the target fatty alcohol ester of α-hydroxy carboxylic acid is produced by converting a lower alkyl ester of α-hydroxy carboxylic acid into a fatty alcohol ester of α-hydroxy carboxylic acid via alcoholysis (i.e., transesterification). The transesterification process is an equilibrium reaction, catalyzed chemically (i.e., with acids or bases) or enzymatically, that is shifted in the desired direction to produce the desired product. One preferred way of shifting the reaction in the direction of the desired product is by reducing the concentration of one of the products (e.g., distillation of a lower-boiling alcohol as soon as it is formed). Another preferred way of shifting the reaction in the direction of the desired product is by increasing the concentration of one of the reactants (e.g., adding more of the starting ester).

In another form of the invention, there is provided a method for synthesizing a fatty alcohol ester of α-hydroxy carboxylic acid, comprising:

converting a lower alkyl ester of α-hydroxy carboxylic acid into a fatty alcohol ester of α-hydroxy carboxylic acid via transesterification, wherein the transesterification process is an equilibrium reaction that is shifted in the desired direction to produce the desired product.

In another form of the invention, there is provided a method for the synthesis of high-purity lauryl lactate comprising:

providing:
a lower-alkyl ester of an α-hydroxy carboxylic acid;
an alcohol; and
an enzyme; and
converting the lower-alkyl ester of an α-hydroxy carboxylic acid into lauryl lactate through transesterification, wherein the transesterification process is an equilibrium reaction that is shifted in the desired direction to produce the desired product.

In another form of the invention, there is provided a fatty alcohol ester of α-hydroxy carboxylic acid formed by converting a lower alkyl ester of α-hydroxy carboxylic acid into a fatty alcohol ester of α-hydroxy carboxylic acid via transesterification, wherein the transesterification process is an equilibrium reaction that is shifted in the desired direction to produce the desired product.

In another form of the invention, there is provided a high-purity lauryl lactate formed by (1) providing a lower-alkyl ester of an α-hydroxy carboxylic acid; an alcohol; and an enzyme; and (2) converting the lower-alkyl ester of an α-hydroxy carboxylic acid into lauryl lactate through transesterification, wherein the transesterification process is an equilibrium reaction that is shifted in the desired direction to produce the desired product.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE INVENTION

The present invention provides a novel approach for the preparation of fatty alcohol esters of α-hydroxy carboxylic acids.

In one form of the invention, the target fatty alcohol ester of α-hydroxy carboxylic acid is produced by converting one ester into another ester via alcoholysis (i.e., transesterification). The transesterification process is an equilibrium reaction, catalyzed chemically (i.e., with acids or bases) or enzymatically, that is shifted in the desired direction to produce the desired product. One preferred way of shifting the reaction in the direction of the desired product is by reducing the concentration of one of the products (e.g., distillation of a lower-boiling alcohol as soon as it is formed). Another preferred way of shifting the reaction in the direction of the desired product is by increasing the concentration of one of the reactants (e.g., adding more of the starting ester).

Figure 1:
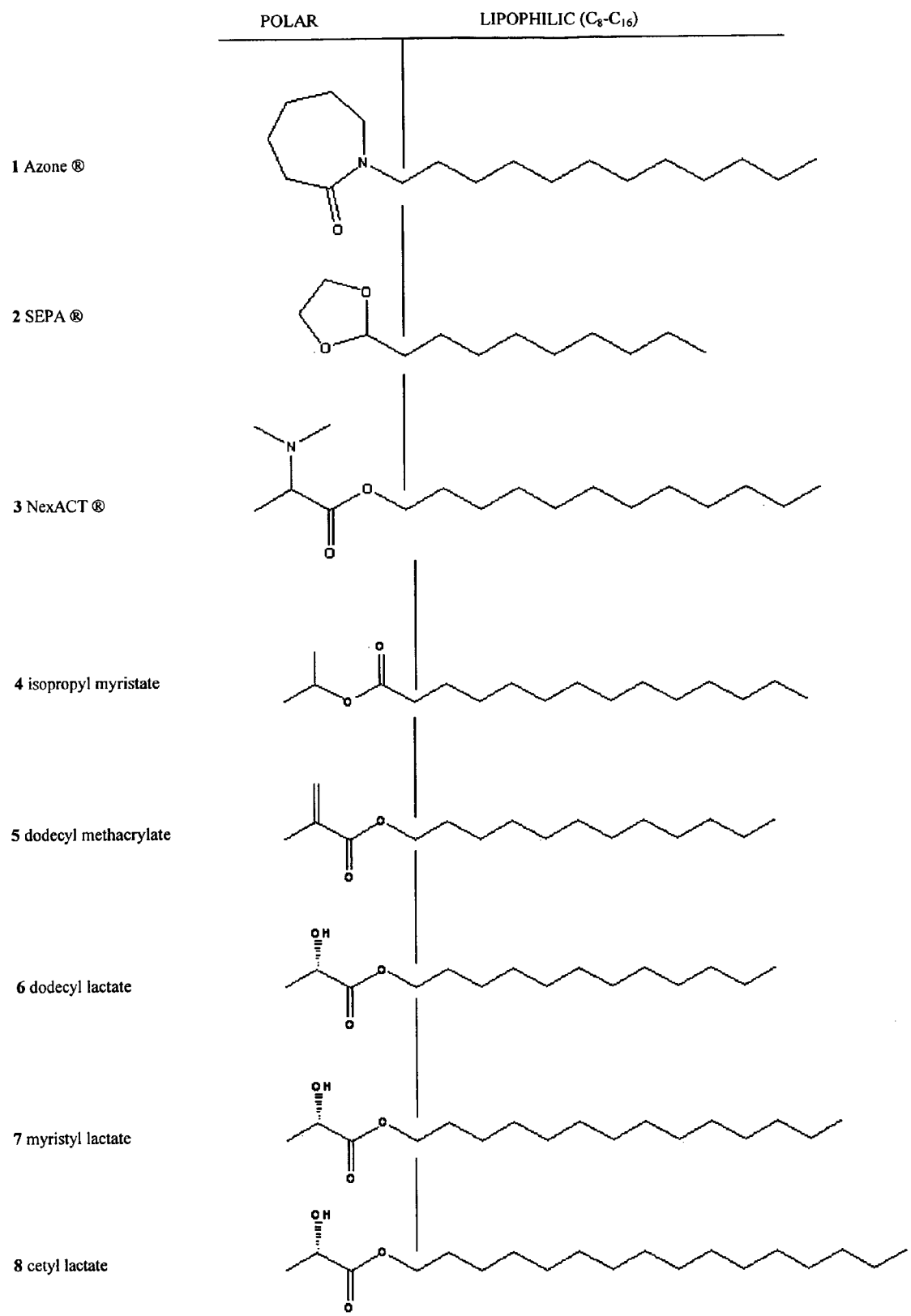
FIG. 1 shows the structures of eight permeation enhancers.
Figure 2:
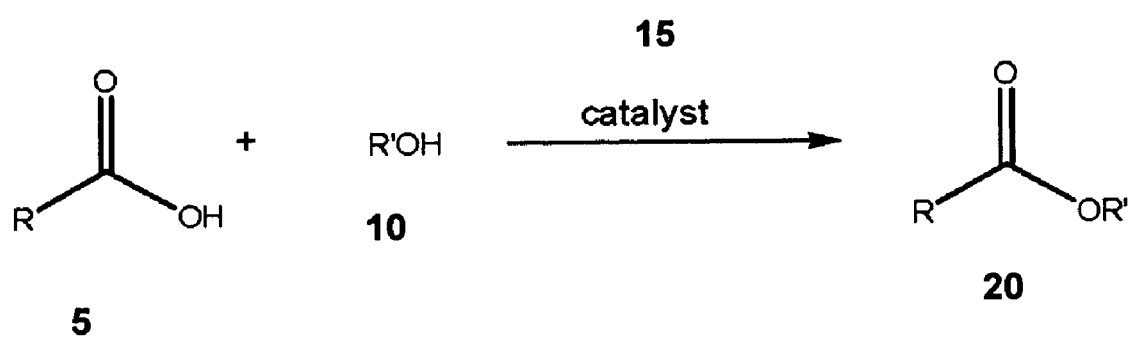
FIG. 2 is an illustration of a process for the preparation of esters using a chemical esterification catalyst (e.g., an organic sulfonic acid or a metal alkylate)
Figure 3:
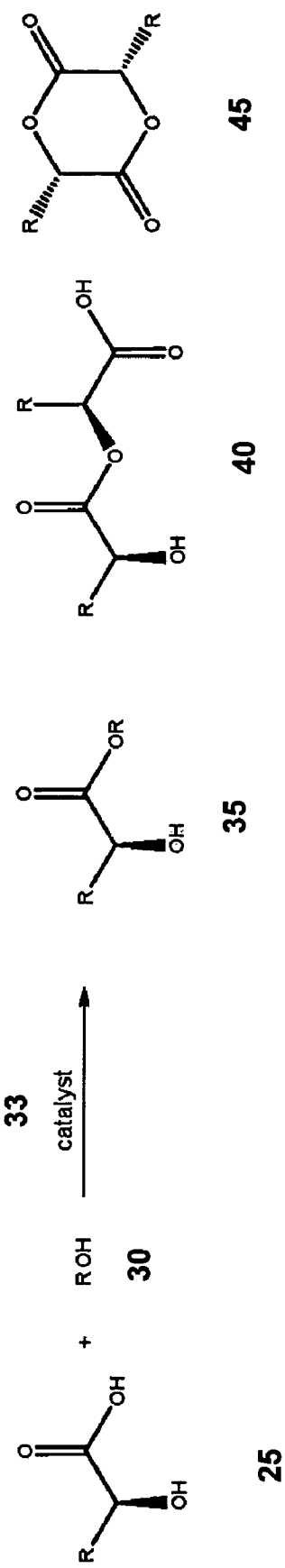
FIG. 3 shows a Fischer-type esterification where an α-hydroxy carboxylic acid is converted into an ester in the presence of alcohol and a chemical esterification catalyst.
Figure 4:
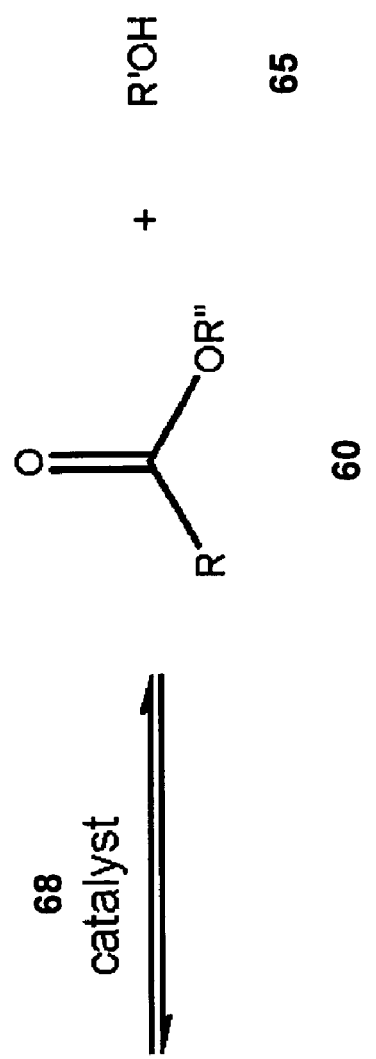
FIG. 4 illustrates a transesterification process in general.
Figure 4:
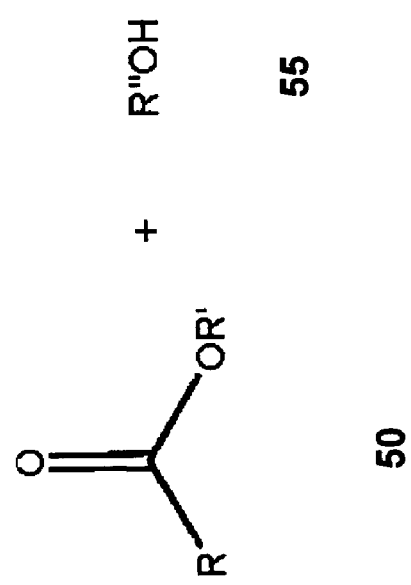

Looking next at FIG. 4, there is shown a general transesterification process. More particularly, in such a process, an ester 50 and alcohol 55 are converted into an ester 60 and alcohol 65 using a catalyst 68 to drive the reaction.

Figure 5:
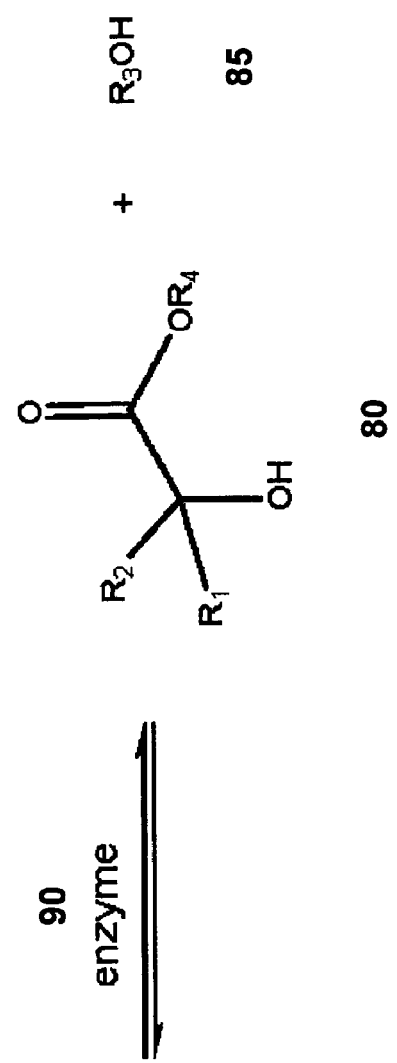
FIG. 5 shows the transesterification process of the present invention.
Figure 5:
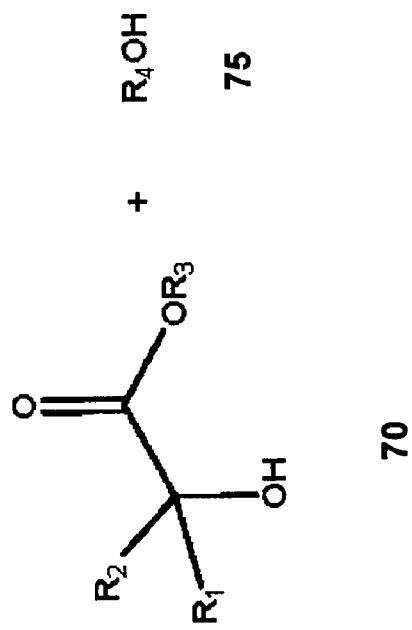

Looking next at FIG. 5, the present invention utilizes a similar transesterification process to produce the target fatty alcohol ester of α-hydroxy carboxylic acid. More particularly, lower-alkyl esters of α-hydroxy carboxylic acids 70 and primary or secondary alcohols 75 are converted into fatty alcohol esters 80 and alcohol 85 using an appropriate chemical (i.e., acid or base) or enzyme 90 to catalyze the reaction.

The transesterification process of the present invention offers several distinct advantages:

(i) the starting reagents (i.e., lower-alkyl esters of α-hydroxy carboxylic acids 70) are relatively inexpensive, readily available, and of good quality and high purity;

(ii) the product fatty alcohol esters 80 are of high purity (i.e., >95%); and (iii) the process is amenable to scaling upward.

Various esters of α-hydroxy carboxylic acids 70 may be used. Some preferred esters of α-hydroxy carboxylic acids 70 are those where:

(i) $R_1$ is one of the following: H, straight chained or branched alkyl, cycloalkyl, substituted alkyl, arylalkyl, aryl, substituted aryl, and heteroaryl;

(ii) $R_2$ is either H or alkyl; and (iii) $R_3$ is one of the following: $C_1$-$C_4$ (e.g., methyl, ethyl, 2,2,2-trifluoroethyl, vinyl, propyl, isopropyl, isopropenyl, butyl, isobutyl, sec-butyl or tert-butyl).

In particular, the ethyl esters of glycolic acid, lactic acid, mandelic acid, 2-hydroxyisobutyric acid, and 2-hydroxycaproic acid are preferred.

Various alcohols 75 may be used. Some preferred alcohols 75 are straight-chain alcohols where $R_4$ is an alkyl group greater than or equal to an eight carbon chain (i.e., $\geqq C_8$). Other suitable alcohols can be primary or secondary, can be branched, can contain various substituents (other than hydroxyl), and can be monounsaturated or polyunsaturated.

In particular, fatty alcohols such as 1-dodecanol, 2-dodecanol, 1-tetradecanol, and 1-hexadecanol are preferred.

Various chemicals (i.e., acids or bases) and enzymes 90 may be used. Some preferred enzymes are lipases. In particular, lipases obtained from the following well-known microorganisms are preferred: *Aspergillus* species, *Rhizopus* species, *Penicillum* species, *Candida* species, *Pseudomonas* species, *Mucor* species, and *Humicola* species.

It is preferred (but not necessarily required) that the lipase be immobilized by attachment to a suitable water-insoluble inorganic or organic material such as silica, ion exchange resins, acrylate resins, porous polystyrene, etc.

The transesterification process is an equilibrium reaction, catalyzed chemically (i.e., with acids or bases) or enzymatically, that is shifted in the desired direction to produce the desired product. One preferred way of shifting the reaction in the direction of the desired product is by reducing the concentration of one of the products (e.g., distillation of a lower-boiling alcohol as soon as it is formed). Another preferred way of shifting the reaction in the direction of the desired product is by increasing the concentration of one of the reactants (e.g., adding more of the starting ester).

In one preferred form of the invention, the transesterification reaction is conducted in such a way that alcohol formed in the course of the reaction is removed from the reaction medium. Alcohol removal can be accomplished in a variety of ways apparent to those skilled in the art including, but not limited to evaporation under ambient conditions, evaporation facilitated by heat, convection, inert gas flow, application of vacuum, distillation (including azeotropic and vacuum distillation, chemical or enzymatic modification, adsorption, etc.

The transesterification reaction of the present invention can also be accomplished by any technique that facilitates the interaction of the reactants and results in the formation of product and the generation of alcohol.

In one embodiment, the reactants (i.e., the lower-alkyl ester of α-hydroxy carboxylic acid 70 and the alcohol 75) are combined such that the amount of ester present relative to the amount of alcohol present is at least an equimolar amount, and may represent a two-to-tenfold or higher molar excess. The reactants are combined in a vessel of appropriate size and design such that controlled heating and stirring is allowed, and from which the reaction mixture can be easily removed. The enzyme 90 is added in an amount that is typically between about 0.10 to about 2 times the weight of the alcohol 75. The reactants are stirred at an appropriate speed for twelve to forty-eight hours with controlled heating from about 30-90° C.

In another embodiment of the present invention, the reactants (i.e., the lower-alkyl ester of α-hydroxy carboxylic acid 70 and the alcohol 75) are combined such that the amount of ester present relative to the amount of alcohol present is at least an equimolar amount, and may represent a two-to-tenfold or higher molar excess. The reactants are combined in a vessel of appropriate size and design such that controlled heating and stirring is allowed, and from which the reaction mixture can be easily removed. The enzyme 90 is added in an amount that is between about 0.10 to about 2.0 times the weight of the alcohol 75. In this embodiment, a fourth substance, i.e., an absorbing agent (e.g. molecular sieves, silica gel, etc.), is added in an amount that is between two to five times the weight of the alcohol. The reactants are stirred at an appropriate speed for twelve to forty-eight hours with controlled heating from about 30-90° C.

In another embodiment of the present invention, the reactants (i.e., the lower-alkyl ester of α-hydroxy carboxylic acid 70 and the alcohol 75) are combined such that the amount of ester present relative to the amount of alcohol present is at least an equimolar amount, and may represent a two-to-tenfold or higher molar excess. The reactants are combined in a vessel of appropriate size and design such that controlled heating and stirring is allowed, and from which the reaction mixture can be easily removed. The enzyme 90 is added in an amount that is between about 0.10 to about 2.0 times the weight of the alcohol. An absorbing agent (e.g., molecular sieves, silica gel, etc.) may be added in an amount that is between two to five times the weight of the alcohol 75. The reactants are stirred at an appropriate speed for twelve to forty-eight hours with controlled heating from about 30-90° C. The alcohol generated during the reaction is removed by distillation by reducing the pressure in the system through the application of a weak vacuum.

In another embodiment of the present invention, the reactants (i.e., the lower-alkyl ester of α-hydroxy carboxylic acid 70 and the alcohol 75) are combined such that the amount of ester present relative to the amount of alcohol present is at least an equimolar amount, and may represent a two-to-tenfold or higher molar excess. The reactants are combined in a vessel of appropriate size and design such that controlled heating and stirring is allowed, and from which the reaction mixture can be easily removed. In this embodiment, a solvent is added in a volume of 100-1000 ml/mole of alcohol. Suitable solvents include acetone, acetonitrile, dioxane, heptane, hexanes, and tetrahydrofuran. The enzyme 90 is added in an amount that is between about 0.10 to about 2.0 times the weight of the alcohol 75. An absorbing agent (e.g., molecular sieves, silica gel, etc.) may be added in an amount that is between two to five times the weight of the alcohol. The reactants are stirred at an appropriate speed for twelve to forty-eight hours with controlled heating from about 30-90° C. The alcohol generated during the reaction is removed by co-distillation with solvent by reducing the pressure in the system through the application of a weak vacuum. Additional solvent is added to the system at approximately the same rate as distillate is formed.

In another embodiment of the present invention, the reactants (i.e., the lower-alkyl ester of α-hydroxy carboxylic acid 70 and the alcohol 75) are combined in a vessel of appropriate size and design such that controlled heating and stirring is allowed, and from which the reaction mixture can be easily removed. The alcohol 75 and enzyme 90 are combined such that the enzyme is present in an amount that is between about 0.10 to about 2.0 times the weight of the alcohol. A solvent is added in a volume of 100-1000 ml/mole of alcohol. Suitable solvents include acetone, acetonitrile, dioxane, heptane, hexanes, and tetrahydrofuran. An absorbing agent (e.g., molecular sieves, silica gel, etc.) may be added in an amount that is between two to five times the weight of the alcohol. The reactants are stirred at an appropriate speed with controlled heating from about 30-90° C. while reducing the pressure in the system through the application of a weak vacuum. The ester 70 is added slowly by means of an addition funnel or syringe pump until an equimolar amount or slight molar excess of ester has been added. The alcohol 85 generated during the reaction is removed by co-distillation with solvent. Additional solvent is added to the system at approximately the same rate as distillate is formed.

In another embodiment of the present invention, the reactants (i.e., the lower-alkyl ester of α-hydroxy carboxylic acid 70 and the alcohol 75) are combined in a vessel of appropriate size and design such that controlled heating and stirring is allowed, and from which the reaction mixture can be easily removed. The ester 70 and enzyme 90 are combined such that the quantity of ester is an amount that represents a two-to-tenfold or higher molar excess based on the quantity of alcohol 75 to be used. The enzyme 90 is present in an amount that is between about 0.10 to about 2.0 times the weight of the alcohol to be used. Optionally, a solvent is added in a volume of 100-1000 ml/mole of alcohol to be used. Suitable solvents include acetone, acetonitrile, dioxane, heptane, hexanes, and tetrahydrofuran. An absorbing agent (e.g., molecular sieves, silica gel, etc.) may be added in an amount that is between two to five times the weight of the alcohol. The reactants are stirred at an appropriate speed with controlled heating from about 30-90° C. while reducing the pressure in the system through the application of a weak vacuum. The alcohol 75 is added slowly by means of an addition funnel or syringe pump. The alcohol 85 generated during the reaction is removed by distillation or co-distillation with a solvent. As needed, additional solvent is added to the system at approximately the same rate as distillate is formed.

In another embodiment of the present invention, the reactants (i.e., the lower-alkyl ester of α-hydroxy carboxylic acid 70 and the alcohol 75) are combined in a vessel of appropriate size and design such that controlled heating and stirring is allowed, the ester 70 and alcohol 75 are combined such that the quantity of ester used is an amount that represents a two-to-tenfold or higher molar excess based on the quantity of alcohol. The mixture is maintained at about 50-90° C. while stirring, and liquid from the reservoir is pumped continuously through a column packed with immobilized enzyme 90 and maintained at about 50-70° C., then returned to the reservoir. Alcohol 85 produced during the reaction in the packed-bed column reactor is removed from the reservoir through evaporation or distillation by reducing the pressure in the reservoir by the application of a weak vacuum.

In another embodiment of the present invention, a mixture of alcohol 75 (X moles), ester 70 (1-5X moles), enzyme 90 (0.6×186.34X), and molecular sieves (5×186.34X), is placed in a stainless steel container of appropriate size such that the bed depth of the mixture does not exceed 1.5", with a preferred depth of 1". The container is placed in a convection oven at 60±5° C. for a time sufficient to consume greater than 95% of the alcohol 75. The time required is dependent upon the reaction size, and may be determined by monitoring the reaction periodically by high performance liquid chromatography (HPLC) or gas chromatography (GC).

In another embodiment of the present invention, a mixture of alcohol 75 (1-dodecanol, X moles), ester 70 (ethyl lactate, 5X moles), enzyme 90 (Novozym® 435, 0.6×186.34X), and molecular sieves (5×186.34X) is placed in a stainless steel container of appropriate size such that the bed depth of the mixture does not exceed 1.5", with a preferred depth of 1". The container is placed in a convection oven at 60° C. for a time sufficient to consume greater than 98% of the 1-dodecanol. The time required is dependent upon the reaction size, and may be determined by monitoring the reaction periodically by HPLC-RI. Once the reaction has progressed satisfactorily, the container is removed from the oven and, after cooling to ambient temperature, the contents of the container are transferred to a larger container for the purpose of adding solvent. Adequate solvent is added to the container so that most of the product is solubilized. Solvents may be chosen from the group of lower molecular weight hydrocarbons, which may include pentane, petroleum ether, hexanes, heptane and isooctane. The solution of product in the hydrocarbon solvent is isolated by vacuum filtration, and transferred to a separatory funnel of adequate size to allow washing with an equal volume of water. The water wash is repeated two more times, and then the organic phase is washed with brine. The final organic solution is dried over magnesium sulfate to remove residual water. At this point, activated carbon may be added so as to render the solution nearly colorless. The dried, carbon-treated solution is isolated by vacuum filtration employing a filtration aid, preferably Celite®. The solution is concentrated by rotary evaporation until most of the solvent has been removed. Residual solvent can be removed by storing the product under vacuum, preferably 29" Hg, preferably at a temperature not to exceed 30° C.

In another embodiment of the present invention, a multi-kilogram batch of lauryl lactate is produced in the absence of molecular sieves. The process involves a mixture of alcohol 75 (1-dodecanol, 4000 mL), ester 70 (ethyl lactate, 4000 mL, 2 molar equivalents), and enzyme 90 (Novozym® 435, 1000 g). The mixture is placed in a 50 L glass pilot plant reactor and is stirred at 60±5° C. for 28-32 hours. (Note: the time required may be determined by monitoring the reaction periodically by HPLC-RI or GC-FID.) Once the reaction has progressed satisfactorily, the reaction mixture is filtered through a semipermeable nylon bag to isolate the enzyme, and the filtrate is returned to the reactor where it is diluted with petroleum ether (4 L). The mixture is washed with brine (2 L) by adding the brine to the reactor, stirring for 1-2 minutes, allowing phase separation to occur, and then drawing off the lower aqueous phase to waste. The brine wash is repeated, and then the mixture is washed with water (4×2 L) in similar fashion. After the final water wash, the mixture is washed again with brine (2 L). Then $MgSO_4$ (100 g) and activated carbon (50 g) are added to the washed organic mixture, and the mixture is stirred for 1 hour at room temperature (RT). The mixture is filtered through a glass fiber filter and the filtrate is concentrated by rotary evaporation until most of the solvent has been removed. Residual solvent can be removed by storing the product under vacuum, preferably 29" Hg, preferably at a temperature not to exceed 30° C.

The following non-limiting examples provide methods for preparing fatty alcohol esters of α-hydroxy carboxylic acids. The specific examples that follow are representative of the potential of the present invention and are not to be construed as limiting the invention in sphere or scope. The methods may be adapted to variation in order to produce products embraced by this invention but not specifically disclosed. Further variations of the methods to produce the same products in somewhat different fashion will be evident to one skilled in the art.

EXAMPLE 1

A mixture of enzyme (275.07 g; lipase B from *Candida antarctica* immobilized on macroporous acrylic resin beads; Novozym® 435), molecular sieves (2301 g), 1-dodecanol (551 mL), and ethyl lactate (1400 mL) in a 12"×20" stainless steel tray (bed depth 1.25") was maintained at 60° C. in a convection oven for 32 hour. Upon work-up, 538 g of lauryl lactate (83% yield) was obtained as a pale yellow liquid. The purity of the product was >95% as assessed by HPLC-RI.

EXAMPLE 2

A mixture of Novozym® 435 (2.21 g), molecular sieves (18.60 g), 1-dodecanol (3.76 g), and ethyl mandelate (3.61 g) in a 150 mL beaker was maintained at 60° C. in a convection oven for 28 hours. Upon work-up, 4.0 g of lauryl mandelate (56% yield) was obtained as a clear viscous liquid. The purity of the product was >95% as assessed by HPLC-DAD.

EXAMPLE 3

A mixture of Novozym 435 (2.81 g), molecular sieves (23.17 g), 3,7-dimethyl-1-octanol (4.64 g), and ethyl lactate (14.78 g) in a 250 mL beaker was maintained at 60° C. in a convection oven for 28 hours. Upon work-up, 4.2 g of 3,7- dimethyl-1-octyl lactate (62% yield) was obtained as an amber-colored liquid. The purity of the product was >96% as assessed by HPLC-RI.

EXAMPLE 4

A mixture of Novozym® 435 (2.43 g), molecular sieves (20.17 g), 1-octadecanol (4.04 g), and ethyl lactate (8.86 g) in a 150 mL beaker was maintained at 60° C. in a convection oven for 28 hours. Upon work-up, 2.0 g of cetyl lactate (40% yield) was obtained as a waxy white solid. The purity of the product was >98% as assessed by HPLC-RI.

EXAMPLE 5

A mixture of Novozym® 435 (1 kg), 1-dodecanol (2000 mL), and ethyl lactate (2000 mL) in a 50 L reactor was stirred (~200 rpm) at 60±5° C. for 28 hours. Upon work-up, 2000 g of lauryl lactate (80% yield) was obtained as a pale yellow liquid. The purity of the product was >97% as assessed by GC.

EXAMPLE 6

A mixture of Novozym® 435 (8.02 g), 1-dodecanol (13.01 g), ethyl lactate (8.70 mL) and acetonitrile (8.70 mL) was placed in a 100 mL three-neck, round bottom flask containing a stir bar. The flask was equipped with an addition funnel charged with acetonitrile, a stopper, and a short path distillation head, which was connected to a vacuum pump. The flask was placed in an oil bath, and the mixture was magnetically stirred at 80±5° C. Additional acetonitrile was added as needed based upon the amount of distillate collected. After 42 hours, analysis of the reaction mixture by GC-FID indicated >96% lauryl lactate.

EXAMPLE 7

A mixture of Novozym® 435 (8.01 g), 1-dodecanol (18.63 g), and hexanes (50 mL) was placed in a 250 mL three-neck, round bottom flask containing a stir bar. The flask was equipped with an addition funnel charged with ethyl lactate (25 mL), a stopper, and a short path distillation head, which was connected to a vacuum pump. The flask was placed in an oil bath, and the mixture was magnetically stirred at 80±5° C. As distillate began to collect, the slow dropwise addition of ethyl lactate was begun. Additional hexanes were added as needed. After 42 hours, analysis of the reaction mixture by GC-FID indicated >95% lauryl lactate.

EXAMPLE 8

A mixture of Novozym® 435 (5.99 g), 1-dodecanol (14.01 g), and hexanes (40 mL) was placed in a 250 mL three-neck, round bottom flask containing a stir bar. The flask was equipped with an addition funnel charged with hexanes, a rubber septum, and a short path distillation head, which was connected to a vacuum pump via an acetone-dry ice condenser. Ethyl lactate (15 mL) was drawn into a 20 mL syringe, which was secured in a syringe pump. The pump was programmed to deliver 10 mL of ethyl lactate at a rate of 1.0 mL/h. The syringe needle was inserted through the rubber septum, and the flask was placed in an oil bath. The mixture was magnetically stirred at 80±5° C. As distillate began to collect, the addition of ethyl lactate was begun. Hexanes were added dropwise at a rate approximating the rate at which distillate was collected. After 12 hours, all devices were turned off and the reaction mixture stood overnight at room temperature (RT). Analysis of the reaction mixture by GC-FID indicated >95% lauryl lactate.

EXAMPLE 9

Novozym® 435 (250-300 g), molecular sieves (2250-2350 g), 1-dodecanol (540-560 mL), and ethyl lactate (1350-1450 mL) were mixed together in a 12"×20" stainless steel tray (bed depth ~1.25"). A total of four trays were prepared in parallel, and maintained at 60° C. in a convection oven for 32 hours. After cooling to ambient temperature, the contents of each tray were diluted with petroleum ether, and the enzyme/sieves mixture was removed by vacuum filtration. The combined filtrates were transferred to a 50 L reactor and processed accordingly. Upon work-up, 2024 g of lauryl lactate (78% yield) was obtained as a pale yellow liquid. The purity of the product was >98% as assessed by HPLC-RI.

EXAMPLE 10

A mixture of Novozym® 435 (500 g), 1-dodecanol (2000 mL), and ethyl lactate (2000 mL) in a 5 L reactor was stirred (~200 rpm) at 60±5° C. for 28 hours. Upon work-up, 2000 g of lauryl lactate (>80% yield) was obtained as a pale yellow liquid. The purity of the product was >95% as assessed by GC-FID.

EXAMPLE 11

A mixture of Novozym® 435 (1 kg), 1-dodecanol (4000 mL), and ethyl lactate (4000 mL) in a 50 L reactor was stirred (~200 rpm) at 60±5° C. for 28 hours. Upon work-up, 4000 g of lauryl lactate (80% yield) was obtained as a pale yellow liquid. The purity of the product was >97% as assessed by GC.

Modifications

It is to be understood that the present invention is by no means limited to the particular constructions herein disclosed and/or shown in the drawings, but also comprises any modifications or equivalents within the scope of the invention.

What is claimed is:

1. A method for synthesizing a fatty alcohol ester of an α-hydroxy carboxylic acid, the method comprising:
    converting a lower alkyl ester of an α-hydroxy carboxylic acid with a fatty alcohol (greater than C8) so as to produce a fatty alcohol ester (greater than C8) of an α-hydroxy carboxylic acid via a transesterification process;
    wherein the transesterification process is catalyzed with an enzyme;
    wherein the transesterification process is carried out in an open container; and
    wherein the transesterification process is an equilibrium reaction producing a fatty alcohol ester and an alcohol and wherein the equilibrium is shifted in the direction of the fatty alcohol ester by reducing the concentration of the alcohol product.

2. A method according to claim 1, wherein the enzyme is a lipase.

3. A method according to claim 2, wherein the lipase is obtained from a microorganism selected from the group consisting of: *Aspergillus* species, *Rhizopus* species, *Penicillum* species, *Candida* species, *Pseudomonas* species, *Mucor* species, and *Humicola* species.

4. A method according to claim 2, wherein the lipase is immobilized by attachment to a suitable water-insoluble material.

5. A method according to claim 4, wherein the suitable water-insoluble material is selected from the group consisting of: silica, ion exchange resins, acrylate resins and porous polystyrene.

6. A method according to claim 1, wherein the concentration of the alcohol product of the transesterification process is reduced by using at least one of the following: evaporation under ambient conditions, evaporation facilitated by heat, rotary evaporation, convection, inert gas flow, application of vacuum, vacuum filtration, distillation, azeotropic distillation, vacuum distillation, chemical modification, enzymatic modification and adsorption.

7. A method according to claim 1, wherein the concentration of the alcohol product of the transesterification process is reduced by distillation.

8. A method according to claim 1, wherein the lower alkyl ester of an α-hydroxy carboxylic acid is represented by the following formula:

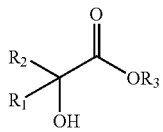

wherein:
$R_1$ is selected from the group consisting of: H, straight chained or branched alkyl, cycloalkyl, substituted alkyl, arylalkyl, aryl, substituted aryl and heteroaryl;
$R_2$ is selected from the group consisting of: H and alkyl; and
$R_3$ is selected from the group consisting of: methyl, ethyl, 2,2,2-trifluoroethyl, vinyl, propyl, isopropyl, isopropenyl, butyl, isobutyl, sec-butyl and tert-butyl.

9. A method according to claim 1, wherein the lower alkyl ester of an α-hydroxy carboxylic acid is selected from the group consisting of: the ethyl esters of glycolic acid, lactic acid, mandelic acid, 2-hydroxyisobutyric acid and 2-hydroxycaproic acid.

10. A method according to claim 1, wherein the fatty alcohol is a straight-chain alcohol represented by the following formula:

$R_4OH$, wherein $R_4$ is an alkyl group greater than an eight carbon chain.

11. A method according to claim 1, wherein the fatty alcohol is selected from the group consisting of primary, secondary, branched, monounsaturated and polyunsaturated alcohols.

12. A method according to claim 1, wherein the fatty alcohol contains a substituent in addition to the hydroxyl moiety.

13. A method according to claim 1, wherein the fatty alcohol is selected from the group consisting of: 1-dodecanol, 2-dodecanol, 1-tetradecanol, 1-hexadecanol, 3,7-dimethyl-1-octanol and 1-octadecanol.

14. A method according to claim 1, wherein the fatty alcohol ester of α-hydroxy carboxylic acid is lauryl lactate.

15. A method according to claim 14, wherein the lauryl lactate has a purity >95%.

16. A method for the synthesis of high-purity lauryl lactate, the method comprising:
a batch process providing:
a lower-alkyl ester of lactic acid;
an alcohol, wherein the alcohol is 1-dodecanol; and
an enzyme; and
converting the lower-alkyl ester of lactic acid with the 1-dodecanol in the presence of the enzyme so as to produce the desired lauryl lactate through a transesterification process;
wherein the transesterification process is carried out in an open container; and
wherein the transesterification process is an equilibrium reaction producing a lauryl lactate and an alcohol and wherein the equilibrium is shifted in the direction of the lauryl lactate by reducing the concentration of the alcohol product.

17. A method according to claim 16, wherein the enzyme is a lipase.

18. A method according to claim 17, wherein the lipase is obtained from a microorganism selected from the group consisting of: *Aspergillus* species, *Rhizopus* species, *Penicillum* species, *Candida* species, *Pseudomonas* species, *Mucor* species, and *Humicola* species.

19. A method according to claim 17, wherein the lipase is immobilized by attachment to a suitable water-insoluble material.

20. A method according to claim 19, wherein the suitable water-insoluble material is selected from the group consisting of: silica, ion exchange resins, acrylate resins and porous polystyrene.

21. A method according to claim 16, wherein the concentration of the alcohol product of the transesterification process is reduced by using at least one of the following: evaporation under ambient conditions, evaporation facilitated by heat, rotary evaporation, convection, inert gas flow, application of a vacuum, vacuum filtration, distillation, azeotropic distillation, vacuum distillation; chemical modification, enzymatic modification and adsorption.

22. A method according to claim 16, wherein the concentration of the alcohol product is reduced by distillation.

23. A method according to claim 16, wherein the lower alkyl ester of lactic acid is represented by the following formula:

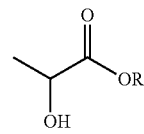

wherein:
R is selected from the group consisting of: methyl, ethyl, 2,2,2-trifluoroethyl, vinyl, propyl, isopropyl, isopropenyl, butyl, isobutyl, sec-butyl and tert-butyl.

24. A method according to claim 16, wherein the lower alkyl ester of lactic acid is selected from the group consisting of: methyl lactate, ethyl lactate, 2,2,2-trifluoroethyl, lactate, vinyl lactate, propyl lactate, isopropyl lactate, isopropenyl lactate, butyl lactate, isobutyl lactate, sec-butyl lactate, and tert-butyl lactate.

25. A method according to claim 16, wherein the alcohol is a straight-chain alcohol represented by the following formula:

$C_{12}H_{25}OH$.

26. A method according to claim 16, wherein the lauryl lactate has a purity >95%.

27. A method according to claim 2, wherein the lipase is not immobilized.

28. A method according to claim 17, wherein the lipase is not immobilized.

29. A method according to claim 1, wherein the fatty alcohol ester of α-hydroxy carboxylic acid is lauryl mandelate.

30. A method according to claim 1, wherein the fatty alcohol ester of α-hydroxy carboxylic acid is 3,7-dimethyl-1-octyl lactate.

31. A method according to claim 1, wherein the fatty alcohol ester of α-hydroxy carboxylic acid is cetyl lactate.

32. A method according to claim 1, wherein the lower alkyl ester of an α-hydroxy carboxylic acid is ethyl lactate.

33. A method according to claim 1, the method comprising converting the lower alcohol in the presence of an absorbing agent.

34. A method according to claim 16, the method comprising converting the lower alcohol in the presence of an absorbing agent.

35. A method according to claim 1, the method comprising converting the lower alcohol in the presence of a solvent.

36. A method according to claim 35, wherein the solvent is selected from a group consisting of the following: acetone, acetonitrile, dioxane, heptane, hexanes and tetrahydrofuran.

37. A method according to claim 16, the method comprising converting the lower alcohol in the presence of a solvent.

38. A method according to claim 37, wherein the solvent is selected from a group consisting of the following: acetone, acetonitrile, dioxane, heptane, hexanes and tetrahydrofuran.

39. A compound, wherein the compound is 3,7-dimethyl-1-octyl lactate.

40. The method of claim 1, wherein the reaction is carried out on at least 200 g of the fatty alcohol.

41. The method of claim 40, wherein the reaction is carried out on at least 400 g of the fatty alcohol.

42. The method of claim 16, wherein the reaction is carried out on at least 200 g of the fatty alcohol.

43. The method of claim 42, wherein the reaction is carried out on at least 400 g of the fatty alcohol.

44. A method according to claim 1, wherein one of the products of the transesterification process is an alcohol and the concentration of the alcohol product is reduced by evaporation under ambient conditions.

45. A method according to claim 1, wherein one of the products of the transesterification process is an alcohol and the concentration of the alcohol product is reduced by evaporation facilitated by heat.

46. A method according to claim 1, wherein one of the products of the transesterification process is an alcohol and the concentration of the alcohol product is reduced by rotary evaporation.

47. A method according to claim 1, wherein one of the products of the transesterification process is an alcohol and the concentration of the alcohol product is reduced by convection.

48. A method according to claim 1, wherein one of the products of the transesterification process is an alcohol and the concentration of the alcohol product is reduced by inert gas flow.

49. A method according to claim 1, wherein one of the products of the transesterification process is an alcohol and the concentration of the alcohol product is reduced by application of vaccum.

50. A method according to claim 1, wherein one of the products of the transesterification process is an alcohol and the concentration of the alcohol product is reduced by vacuum filtration.

51. A method according to claim 1, wherein one of the products of the transesterification process is an alcohol and the concentration of the alcohol product is reduced by azeotropic distillation.

52. A method according to claim 1, wherein one of the products of the transesterification process is an alcohol and the concentration of the alcohol product is reduced by vacuum distillation.

53. A method according to claim 1, wherein one of the products of the transesterification process is an alcohol and the concentration of the alcohol product is reduced by chemical modification.

54. A method according to claim 1, wherein one of the products of the transesterification process is an alcohol and the concentration of the alcohol product is reduced by enzymatic modification.

55. A method according to claim 1, wherein one of the products of the transesterification process is an alcohol and the concentration of the alcohol product is reduced by adsorption.

56. A method according to claim 1, wherein the fatty alcohol ester of α-hydroxy carboxylic acid is stearyl lactate.

\* \* \* \* \*